United States Patent [19]
Laible et al.

[11] Patent Number: 5,238,655
[45] Date of Patent: * Aug. 24, 1993

[54] APPARATUS FOR COLLECTING BLOOD SAMPLE

[75] Inventors: Rodney Laible, Overland Park, Kans.; Bradley V. Brown, RR. 1, Box 37, Bennington, Nebr. 68007

[73] Assignee: Bradley V. Brown, Bennington, Nebr.

[ * ] Notice: The portion of the term of this patent subsequent to May 5, 2009 has been disclaimed.

[21] Appl. No.: 878,770

[22] Filed: May 5, 1992

Related U.S. Application Data

[63] Continuation-in-part of Ser. No. 549,953, Jul. 9, 1990, Pat. No. 5,110,557.

[51] Int. Cl.⁵ ............................................. B01L 11/00
[52] U.S. Cl. ................................. 422/101; 128/637; 128/763; 128/765; 128/766; 604/76
[58] Field of Search ............... 422/101; 128/637, 760, 128/763, 765, 766; 604/76; 73/864.01, 863.23

[56] References Cited

U.S. PATENT DOCUMENTS

| | | | |
|---|---|---|---|
| 3,113,688 | 12/1963 | Campbell | 604/76 |
| 4,813,931 | 3/1989 | Hauze | 128/760 |

FOREIGN PATENT DOCUMENTS

| | | | |
|---|---|---|---|
| 8802134 | 3/1990 | Netherlands | 128/760 |

*Primary Examiner*—Robert J. Warden
*Assistant Examiner*—Laura E. Collins
*Attorney, Agent, or Firm*—John A. Beehner

[57] ABSTRACT

A blood sample collection apparatus includes a removable plug adapted to fit within the open end of a blood collection tube. A vacuum tube extends through the plug for evacuating air from the collection tube. A pickup tube protrudes outwardly from the plug for supplying blood to a drop tube extending downwardly from the plug with its lower end positioned within the collection tube substantially below the lower end of the vacuum tube. A primary filter is sealed against the underside of the plug to filter the air drawn through the vacuum tube by a portable hand-held vacuum source. The primary filter is a hydrophobic microporous membrane operative to allow airflow therethrough but to block liquid flow therethrough. A secondary filter is operatively interposed between the vacuum tube and he vacuum source for increased safety. Installation of the secondary filter bypasses a bleeder port which renders the apparatus inoperative in the absence of the secondary filter.

11 Claims, 5 Drawing Sheets

APPARATUS FOR COLLECTING BLOOD SAMPLE

CROSS REFERENCE TO RELATED APPLICATION

This application is a continuation-in-part of Application Ser. No. 07/549,953, filed on Jul. 9, 1990 now U.S. Pat. No. 5,110,557.

BACKGROUND OF THE INVENTION

The present invention is directed generally to a blood sample collection apparatus capable of quickly and easily collecting sufficient blood from a puncture site on a patient for testing of the blood and more particularly to such an apparatus which protects the medical attendant from contamination and which assures a high quality blood sample.

Various devices and methods have been used in the past for collecting blood from a puncture site on a patient's finger, ear, heel or other body part. A common apparatus is a small capillary tube which fills with blood by capillary action. These tubes are so small, however, that one cannot collect a sufficient quantity of blood for common blood tests so five or six are generally needed.

Another device for collecting blood samples is a collection tube having a scoop formed on the open end thereof to scoop the blood off of a finger. There are two problems with the use of this device. First, its messy. Blood often runs down the patient's finger and even on the hands of the medical attendant as well, creating exposure to A.I.D.S. and like diseases. Secondly, the sample may be contaminated with tissue fluids from squeezing of the finger. Compression of the finger can cause hemolysis and the release of hemoglobin which can alter blood test results.

Finally, Campbell, U.S. Pat. No. 3,113,688, discloses a blood collector wherein a collection tube is closed with a plug having a hose extended therefrom for evacuating the tube by the medical attendant sucking on the free-end of the hose. Blood collected from a puncture site is deposited into the tube on the underside of the plug adjacent the open end of the tube communicating with the suction hose, such that at least portions of the blood sample may be easily sucked into the medical attendant's mouth. Devices which operate by suction from the mouth of the operator are believed to be prohibited by federal regulations. Guidelines promulgated by the Center for Disease Control on Atlanta, Ga., likewise advise against the use of such devices.

Brown, U.S. Pat. No. 5,110,557, discloses a blood sample collection which is believed to be a marked improvement over the state of the art. The collector of the present invention provides improved primary and secondary filters as well as the safety feature of rendering the collector inoperative in the absence of a secondary filter.

Accordingly, a primary object of the invention is to provide an improved blood sample collection apparatus.

Another object to provide such an apparatus wherein collected blood is deposited into a collection tube near the bottom of the tube in substantial spaced relation below the opening through which a vacuum is applied to the tube to prevent blood from being drawn into the vacuum tube and to the pump.

Another object is to provide such an apparatus wherein blood is deposited adjacent the anticoagulant in the bottom of the tube to bubble the blood to effect mixing with the anticoagulant and prevent clotting.

Another object is to provide a blood sample collection apparatus which may be conveniently held at any desired angle for collecting blood without danger of the blood being drawn into the vacuum source.

Another object is to provide such an apparatus with a filter to block the flow of blood to the vacuum source.

Another object is to provide such an apparatus with a simple yet effective filter that operates regardless of the angle at which the tube is held and regardless of the extent to which the tube is filled within the capacity of the tube.

Another object is to provide such an apparatus including a hand-held reusable vacuum source which may be conveniently and comfortably held in either hand and readily connected to and disconnected from a blood collection tube.

Another object is to provide a blood sample collection apparatus including a disposable plug for use in filling each collection tube.

Another object is to provide such an apparatus wherein the vacuum source includes an electric vacuum pump and a second filter to prevent air born viruses from being spread to the ambient air.

Another object is to provide such an apparatus wherein the primary filter is a gas permeable membrane across the lower end of a disposable plug on the blood collection tube.

Another object is to provide such an apparatus wherein the secondary filter is housed within the reusable vacuum pump apparatus and installed in a manner to render the vacuum pump inoperative in the absence of the secondary filter.

Finally, an object of the invention is to provide a blood sample collection apparatus which is simple and rugged in construction, economical to manufacture and efficient in operation.

SUMMARY OF THE INVENTION

The blood sample collection apparatus of the invention includes a blood collection tube having open and closed ends and a plug adapted to fit within and seal the open end. A vacuum tube extends through the plug for evacuating air from the collection tube. Likewise, a pickup tube protrudes outwardly from the plug for drawing blood from a puncture site. The pickup tube communicates with a drop tube extending downwardly from the plug and having a lower end positioned within the blood collection tube and spaced substantially below the lower end of the vacuum tube. A first filter associated with the plug is operatively interposed between the lower end of the vacuum tube and the air within the blood collection tube for filtering the air drawn through the vacuum tube to prevent blood from being drawn into the vacuum. Finally, a portable hand-held vacuum source is provided for connection to the vacuum tube.

The first filter is preferably a circular disk formed of a hydrophobic microporous membrane which allows gases to pass through but not liquids. This type of filter would be mounted on the lower end of the plug, covering and sealing the vacuum tube but allowing the drop tube to pass through, thus forming a filter seal over the vacuum tube.

A second filter is preferably provided on the hand-held vacuum source to prevent the spread of airborne viruses to the ambient air and as a final screen to keep blood from the vacuum source. This second filter is preferably removably mounted in the device such that it may be replaced if needed. The housing of the hand-held vacuum source may have a bleeder port positioned to establish fluid communication between the vacuum source inlet port and the ambient atmosphere in the absence of a secondary filter thereby rendering the blood collection apparatus inoperative unless the secondary filter is installed therein.

The provision of a hand-held powered vacuum source enables the use of an evacuated tube for collecting blood samples without the danger of exposure of the operator to diseases, as in the case of a hose adapted for suction by mouth. The long drop tube insures that the blood sample will be deposited near the base of the tube where it is least likely to be aspirated into the vacuum source. Furthermore, the long drop tube is operative regardless of the angle at which the collection tube is disposed and furthermore, deposits the blood sample adjacent the anticoagulant to prevent clotting and to assure the high quality of the collected sample. The plug and associated main filter are economically manufactured and are intended to be disposed of after each sanitary single patient usage. The collection tube includes an integral hinged cap operative to close the open end of the tube to prevent spillage of the sample in the centrifuge and while handling and to further minimize air contact with the blood.

DESCRIPTION OF THE PREFERRED EMBODIMENTS

The blood sample collection apparatus 10 of the present invention is illustrated in the drawings as including a blood collection tube 12 having an open end 14 and closed end 16 similar to a conventional test tube but with an integral closure cap 18 connected to the tube by a flexible hinge strap 20 for closing the tube once a sample has been collected. Tube 12 is preferably a 750 microliter tube. Accordingly, a sample which fills between one third and one half of the tube affords sufficient blood for the 250 to 550 microliters required for common tests.

A removable plug 22 fits within and seals the open end 14 of the blood collection tube 12. The plug has a stepped rod shape including a central plug portion 24, an increased diameter top stopper portion 26 which engages the open end of the collection tube 12 to limit the penetration Of the plug portion, and a bottom spacer portion 28 extending into the tube and defining an annular chamber 30 around it. The plug is preferably formed of a resilient rubber-like plastic material to effectively plug the open end of collection tube 12.

Figure 4:
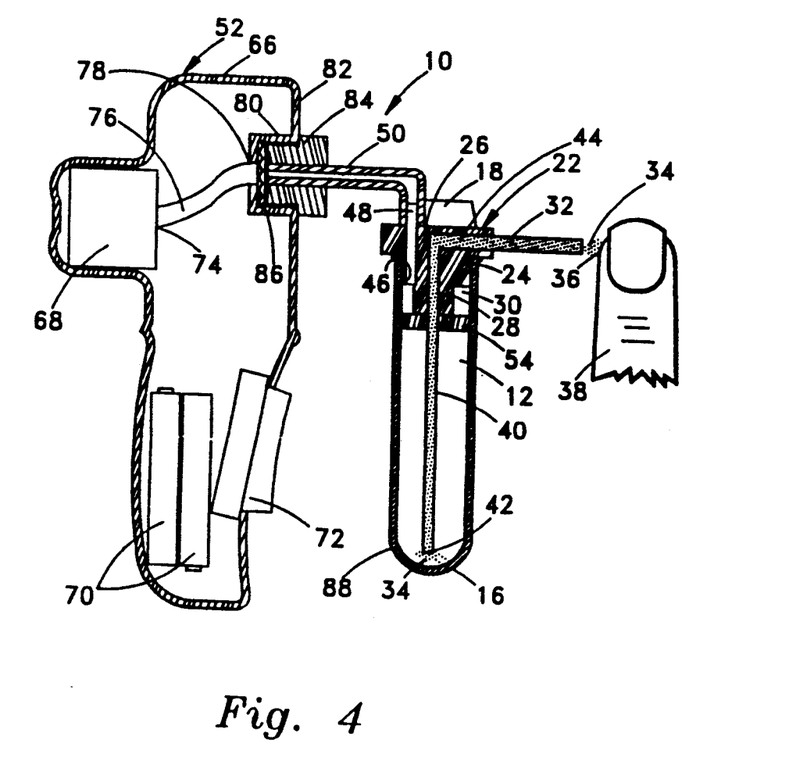
FIG. 4 is a side sectional view of the first embodiment of the invention in use.
Figure 5:
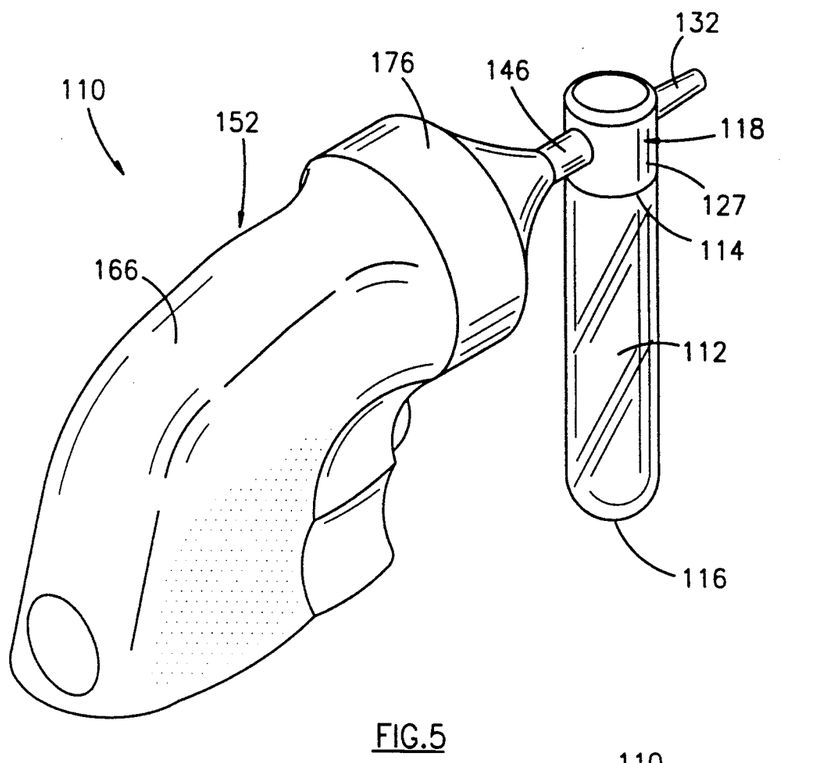
FIG. 5 is perspective view of an alternative embodiment of the blood sample collection apparatus of the invention.

Referring to FIG. 4, a pickup tube 32 protrudes outwardly from stopper portion 26 for drawing blood 34 from a puncture site 36 on a patient's finger 38, earlobe, or other body part. A drop tube 40 extends downwardly through plug spacer portion 28 and has a lower end 42 positioned within the collection tube 12 at a position spaced substantially below the bottom of plug portion 24 through which an opening is provided to the vacuum source as described below. A conduit 44 is provided within plug 22 for connecting the pickup tube 32 and drop tube 40 so that blood drawn into the pickup tube is deposited into the blood collection tube 12 through the lower end of the drop tube 40. Conduit 44 may simply be an L-shaped passageway through which an integral combination pickup tube/drop tube is inserted or may be a passageway into the opposite ends of which separate pickup and drop tubes are inserted. The pickup and drop tubes 32 and 40 are preferably formed of a clear plastic or glass so that the blood sample collection operation can be closely monitored.

A vacuum tube 46 extends vertically through plug 22, the lower end in the preferred embodiment opening through the underside of plug portion 24 as shown best in FIG. 4. A tubular insert 48 protrudes upwardly from the top of the plug for engagement by the inlet spout 50 of a hand-held vacuum source 52. Any type of detachable connection between the hand-held vacuum source and vacuum tube 46 may be provided.

A main filter 54 is provided in the illustrated embodiment in the form of an annular ring in sealing engagement against the underside of plug 22 and having a center opening 56 to accommodate passage of the drop tube 40 therethrough. Filter 54 is preferably made of plastic or other material impervious to fluid flow through the filter. Rather, the exterior surface 58 is roughened to effectively form a plurality of grooves 60 which enable airflow between the filter 54 and interior periphery 62 of collection tube 12. The exterior diameter of filter 54 corresponds to the interior diameter of collection tube 12 so that air passing between the main filter 54 and collection tube is confined to the grooves 60.

Figure 1:
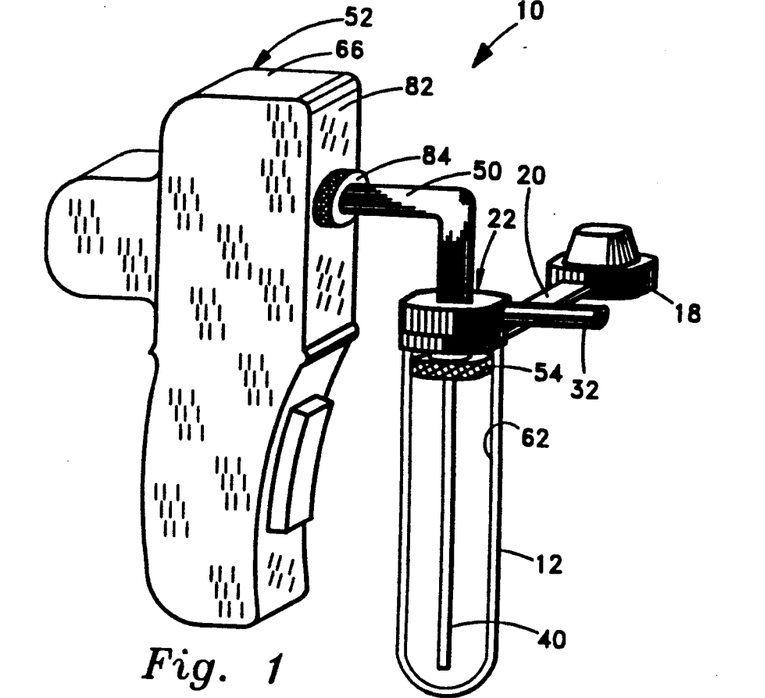
FIG. 1 is a perspective view of a first embodiment of the blood sample collection apparatus of the invention.
Figure 2:
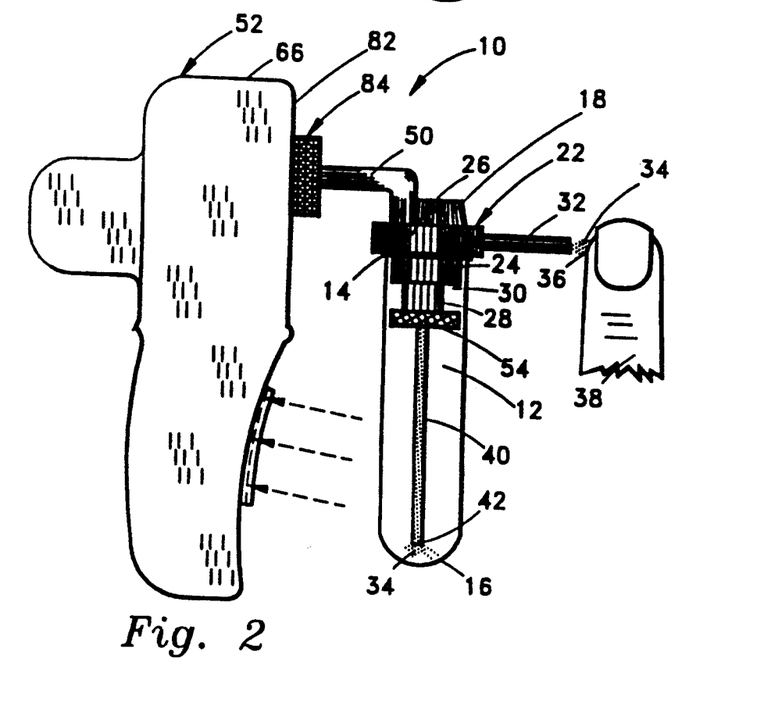
FIG. 2 is a side elevational view of the invention in use.
Figure 3:
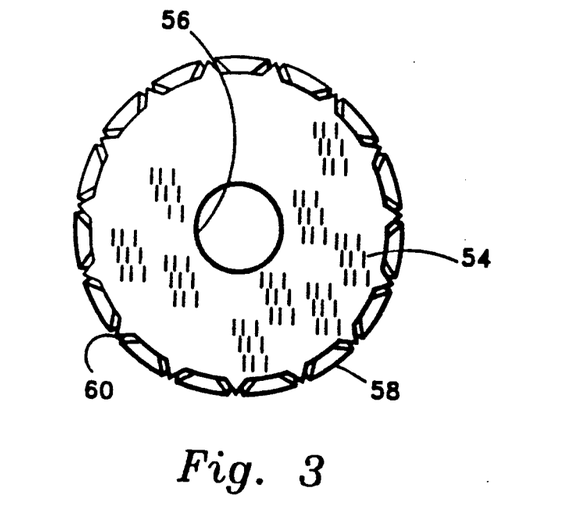
FIG. 3 is an enlarged top plan view of a main filter ring of the invention.

Referring to FIGS. 1 and 2, the pattern of grooves 60 may be crisscrossed as in a knurling pattern. The individual grooves may be arcuate or otherwise shaped so long as they are interconnected and extend from the upper edge to the lower edge of the main filter to enable the passage of air upwardly through the grooves between the main filter and collection tube wall. The main filter as thus formed provides an inexpensive yet effective device for preventing blood from being drawn into the vacuum source 52. This filter is operative regardless of the angle at which the tube is held and regardless of the extent to which the tube is filled within the capacity of the tube. Whereas main filter 54 may be adhered to the underside of plug 22, it is preferably held in place by frictional retention on drop tube 40.

Vacuum is provided from a portable hand-held vacuum source 64 which includes a housing 66 which contains an electric vacuum pump 68 electrically connected to a pair of batteries 70 through an exteriorly accessible trigger switch 72.

Vacuum pump 68 has an inlet 74 connected by conduit 76 to an inlet port 78 embodied in a filter receptacle 80 on housing front wall 82 A conventional fiber disc filter is placed within the receptacle which is threaded for receiving a male threaded retainer 84 for spout 50. A circular fiber disc filter 86 prevents airborne viruses from being spread in the ambient air exhausted by the vacuum pump 68 and also provides a last chance to prevent any blood in the air stream from being aspirated into the vacuum pump 68.

In operation, the blood collection tube 12 is provided with the plug 22, pickup tube 32, drop tube 40 and main filter 54 preassembled for connection as a unit to the vacuum source 64. Furthermore, an anticoagulant may be provided in the bottom of the tube either in the form of a liquid or a coating on the inside of the tube. The spout 50 of the vacuum source is connected to the tubular insert 48 of the vacuum tube 46 as shown in FIG. 4. The patient's finger, ear, or other body part is then pricked to present a droplet of blood. Trigger switch 72 of the vacuum source is depressed to apply a vacuum to the collection tube 12. The pickup tube 32 is moved into engagement with blood droplet to draw blood by the force of the vacuum through the pickup tube 32 and drop tube 40 for deposit at the base of the collection tube 12 in contact with the anticoagulant. The airflow through the tubes bubbles the blood and enhances mixing with the additive. The long length of the drop tube prevents the blood from sticking to the side of the collection tube above the anticoagulant and forming clots. Whereas the actual spacing of the bottom of the drop tube from the bottom surface of the collection tube is not critical to the invention, it is preferred that the spacing be less than a diameter of the collection tube. Accordingly, blood from the drop tube will be directed into contact with the anticoagulant regardless of the angle at which the collection tube is held. This is important because it is not practical to require that the collection tube be vertically disposed in use. The way a patient holds his or her hand may dictate the best angle for the pickup tube to collect the blood so as to prevent blood from running down the finger, causing a mess and possibly exposing the medical attendant to A.I.D.S. Likewise, there is often not enough room for pediatric nurses to hold the collection tube upright when collecting blood from a puncture site on an infant's heel due to positioning in a crib or for other reasons.

Once the blood sample has been collected in the tube 12, plug 22 is removed and disposed of, whereupon the hinged cap 18 is inserted onto the open end of the tube. Cap 18 prevents spillage of the blood during handling of the tube and in the centrifuge. The cap minimizes air contact with the blood and resulting contamination. Since the cap is integral with the tube it won't get lost or misplaced.

In One embodiment, a vacuum pump 68 capable of generating a 12 millimeter mercury capacity vacuum was sufficient for the blood sample collection apparatus to operate effectively. A vacuum force of up to 3 psi or intermittent 8.5 psi is believed to be acceptable.

An alternative embodiment of the blood sample collection apparatus 110 of the present invention is illustrated in FIGS. 5-11 as including a blood collection tube 112 having an open end 114 and a closed end 116 as previously disclosed. A removable plug 118 fits within and seals the open end 114 of the blood collection tube 112. Plug 118 includes a lower end portion 119 adapted to fit within and seal the open end 114 of blood collection tube 112. The lower end portion 119 is a generally tubular member having a divider wall 120 extended thereacross to form a pair of passages 121 and 122. The underside 123 of plug 118 includes a peripheral ridge 124 circumscribing said passages 121 and 122 and another coplanar ridge 125 on the underside of divider wall 120. Plug 118 preferably has an annular shoulder 126 extending outwardly from the upper end of lower end portion 119 to form a top stopper portion 127. The blood collection tube 112 thus may snap-fit onto the lower end portion 119 and be secured in place against shoulder 119, thus forming a substantially liquid-tight seal. The top stopper portion 127 engages the open end 114 of the collection tube 112 to limit the penetration of the lower end portion 119.

The plug 118 is preferably formed of an inexpensive rubber-like plastic material to effectively plug the open end of the collection tube 112 and also to be disposable.

Figure 6:
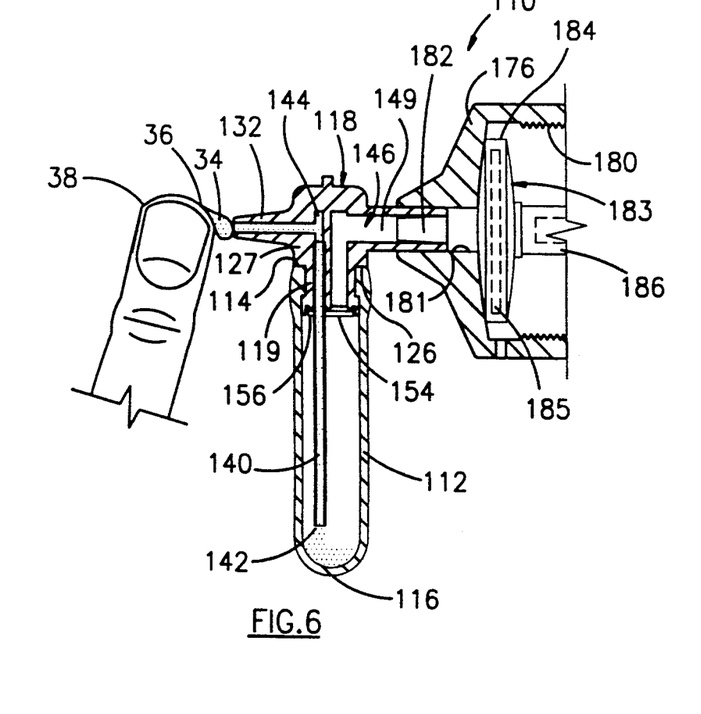
FIG. 6 is a side sectional view of the embodiment of FIG. 5 in use.
Figure 7:
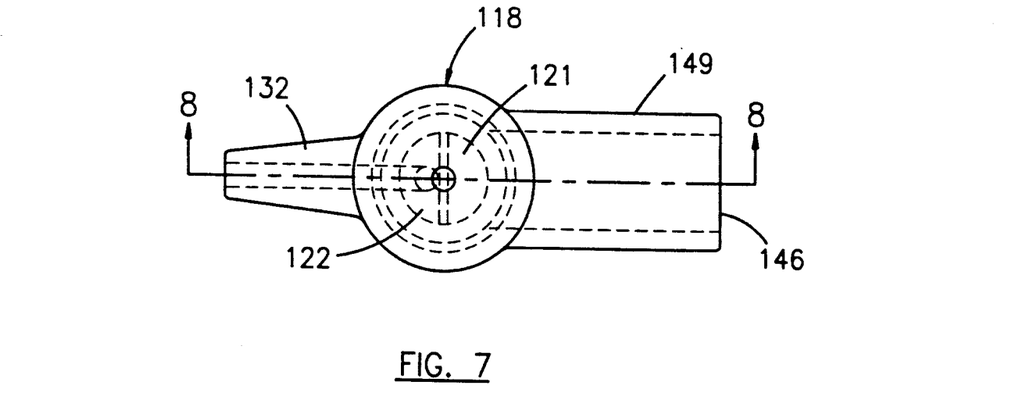
FIG. 7 is a top view of the plug of the alternate embodiment with dotted lines indicating internal structure thereof.
Figure 8:
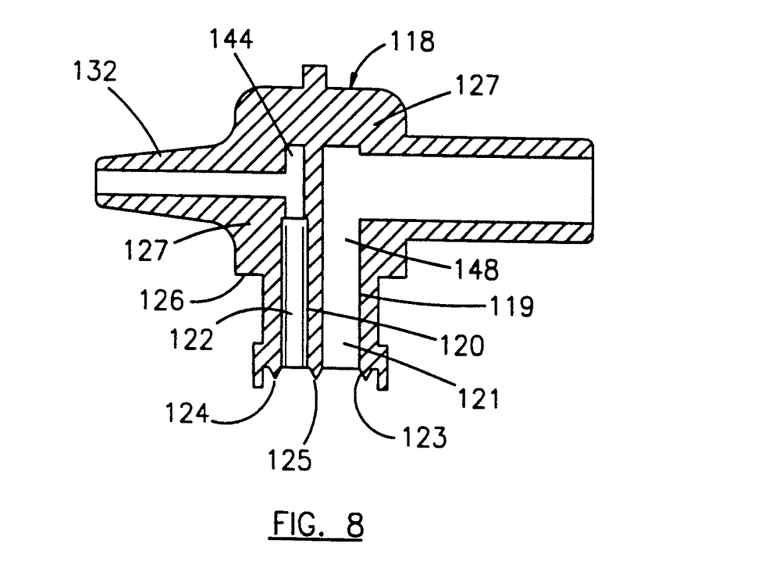
FIG. 8 is a side sectional view of the plug, taken along line 8—8 in FIG. 7.
Figure 9:
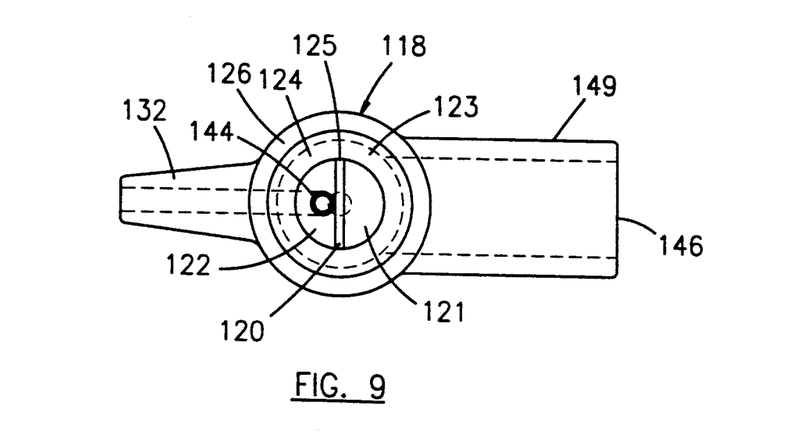
FIG. 9 is a bottom view of the plug with dotted lines indicating internal structure thereof.

Referring to FIG. 6 a pickup tube 132 protrudes outwardly from the top stopper portion 127 for drawing blood 34 from a puncture site 36 on a patient's finger 38, earlobe or other body part. A drop tube 140 extends downwardly through the passage 122 of lower end portion 119 and has a lower end 142 positioned within the collection tube 112 at a position spaced substantially below the underside 143 of the lower end portion 119. A conduit 144 is provided within the removable plug 122 for connecting the pickup tube 132 and drop tube 140 so that blood drawn into the pickup tube is deposited in the blood collection tube 112 through the lower end 142 of the drop tube 140. Passage 122 is the lower end of conduit 144. The conduit 144 is functionally identical to the conduit 44 previously described, as are the pickup and drop tubes 132 and 140 functionally identical to pickup and drop tubes 32 and 40.

An L-shaped Vacuum tube 146 extends through the plug 118 such that the drop tube 140 and the lower vertical section 148 of the vacuum tube 146 are substantially parallel. The upper horizontal section 149 of the vacuum tube 146 is preferably substantially co-linear with the pickup tube 132 and extends in the opposite direction. The plug 122 thus is generally T-shaped. The lower end of the vertical section 148 of the vacuum tube 146 opens through the underside 143 of the plug 118 such that passage 121 is the lower vertical section 148. The horizontal section 149 of the vacuum tube 146 protrudes horizontally from the top stopper portion 127 of the plug 118 for connection to the inlet port 150 of a hand-held vacuum source 152. It is contemplated that this connection between the hand-held vacuum source 152 and the upper horizontal section 149 of the vacuum tube 146 will be an airtight frictional connection.

A primary filter 154 is provided in the illustrated embodiment in the form of a circular disk secured to the underside 143 of 118. An opening 156 in the primary filter 154 is provided to allow the drop tube 140 to protrude therethrough. The primary filter 154 is sealed against the underside 143 of plug 118 such that all air drawn into said vacuum tube 146 from said collection tube 112 must flow through the primary filter 154. Primary filter 154 is sealed by adhesive or the like against ridges 124 and 125 thereby closing and sealing both passages 121 and 122. The side of the filter 154 covering passage 122 is pierced by the drop tube 140, but this does not affect the seal of the filter 154 across the open end of vacuum tube 146. Primary filter 154 could be provided in the shape of a semicircle to seal only the open end of the vacuum tube 146, but installation is facilitated by providing a full circular disk shaped primary filter 154. The main filter 154 is preferably a hydrophobic microporous membrane filter made from polytetrafluoroethylene (PTFE) which allows gas to pass through, but not liquid. Therefore, blood 34 deposited in the blood collection tube 112 through the drop tube 140 cannot be pulled into the vacuum source 152. The main advantage of such a filter is that this filter has been shown to be completely effective in preventing the transmission of infectious blood born viruses such as herpes and HIV.

Figure 10:
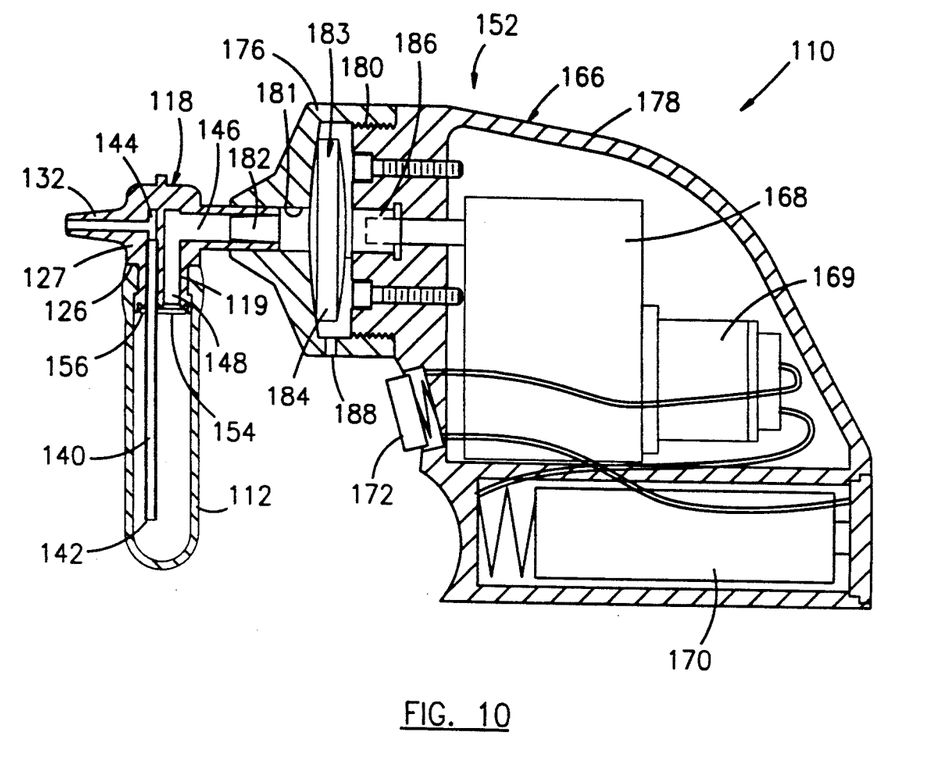
FIG. 10 is a side sectional view of the embodiment of FIG. 5.

Vacuum is provided from a portable hand-held vacuum source 152 which includes a housing 166 which contains an electric vacuum pump 168 driven by electric motor 169 which is electrically connected to a battery 170 through an exteriorly accessible trigger switch 172. The housing 166 is preferably constructed of two sections, a front housing section 176 and a rear housing section 178, which are connected by a set of screw threads 180, shown in FIG. 7, by which the front housing section 176 may be screwed onto the rear housing section 178. As shown in FIG. 10, the upper horizontal section 149 of the vacuum tube 146 protrudes from plug 122 and is fit within a passage 181 in the front housing section 176 of the vacuum source 152.

Within passage 181, vacuum tube 146 is connected to the inlet tube 182 of a secondary filter 183. The secondary filter 183 is preferably a commercially disk filter having inlet tube 182 leading into a filter housing 184 containing a filter media 185 and having an outlet tube 186 adapted for connection to the inlet port 150 of vacuum source 152. The filter media 185 is preferably made of material similar to that used in the primary filter 154. An air inlet tube 187 from vacuum pump 168 protrudes in inlet port 150 for insertion within and connection to the outlet tube 186 of secondary filter 183. When the secondary filter 183 is properly installed as shown in FIG. 10, the vacuum tube 146, the secondary filter 183 and the inlet port 150 for the electric vacuum pump 168 form a fluid-tight conduit for air to pass through.

In the preferred embodiment, a safety device is provided for rendering the blood collection apparatus inoperative in the absence of secondary filter 183. If the secondary filter 183 is not in place, upon activation of the electric vacuum pump 168 ambient air is drawn into the inlet port 150 through a bleeder port 188 (FIG. 10) in the front housing section 176. In the absence of the secondary filter 183, the vacuum created in blood collection tube 112 is so rendered that the device is inoperative for collecting blood as intended. Only when the secondary filter 186 is in place will the blood sample collection apparatus 110 operate correctly.

To facilitate assembly, rear housing section 178 may have a removable front wall 190 held in place by a pair of securement bolts 192A and 192B or any other suitable fasteners.

Figure 11:
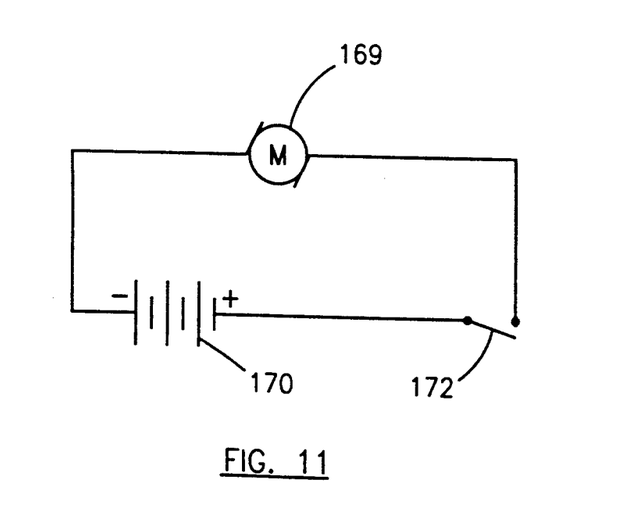
FIG. 11 is a schematic circuit diagram of the embodiment of FIG. 5.

FIG. 11 illustrates a schematic circuit diagram for the blood sample collection apparatus embodiment shown in FIGS. 5-11, consisting of the trigger switch 172, the electric motor 169 and the battery 170, all connected in series.

In operation, the embodiment of FIGS. 5-11 operates substantially similarly to the embodiment of FIGS. 1-4, as previously described. However, safety of the blood sample collection apparatus 110 has been enhanced by the mounting of the secondary filter in a manner to reorder the apparatus inoperative in the absence of the secondary filter.

Thus there has been shown and described a blood sample collection apparatus which accomplishes at least all of the stated objects.

We claim:

1. A blood collection apparatus comprising;
   a blood collection tube having an open end and a closed end;
   a plug having a lower end portion adapted to fit within and seal said open end of said blood collection tube, said plug having an underside substantially spanning said blood collection tube upon fitting the lower end portion of said plug therein,
   a vacuum tube extended through said plug for evacuating air from said blood collection tube, said vacuum tube having an upper end and a lower end opening through the underside of said plug;
   a pickup tube protruding outwardly from said plug for drawing blood from a puncture site;
   a drop tube extending downwardly from said plug and having a lower end positioned within the blood collection tube and spaced substantially below the lower end of the vacuum tube;
   conduit means within said plug for connecting said pickup tube and drop tube so that blood drawn into said pickup tube is deposited in the blood collection tube through the lower end of the drop tube;
   a portable hand-held vacuum source including an inlet port;
   means for connecting said inlet port to the upper end of said vacuum tube for creating a vacuum within said blood collection tube;
   a primary filter comprising a hydrophobic porous membrane operative to allow gas flow therethrough but to block liquid flow therethrough; and
   sealing means for sealing said primary filter against the underside of said plug such that all air drawn into said vacuum tube from said collection tube must flow through said primary filter.

2. The blood collection apparatus of claim 1 wherein said lower end portion comprises a generally tubular member having a divider wall extended thereacross to form a pair of passages therethrough, one passage comprising the lower end of said vacuum tube and the other passage comprising said conduit means, said sealing means being operative to seal said primary filter against said divider wall and generally tubular member.

3. The blood collection apparatus of claim 2 wherein said primary filter covers both passages, said drop tube piercing said primary filter and extending into said other passage for fluid communication with said conduit means.

4. The blood collection apparatus of claim 1 wherein said primary filter comprises a disk having an outer circumference attached to said lower end of said plug, said disk covering and sealing said vacuum tube, said drop tube extending downwards through and beyond said disk such that said disk may not interfere with blood entering said blood collection tube but filtration of air going into said vacuum tube may be accomplished.

5. The blood collection apparatus of claim 1 further comprising,
a secondary filter operatively interposed between said upper end of said vacuum tube and said inlet port of said vacuum source, said secondary filter comprising a filter disk of a hydrophobic porous membrane and being operative to allow gas flow therethrough but to block liquid flow therethrough, thus further filtering air drawn through said vacuum tube.

6. A blood collection apparatus comprising:
a blood collection tube having an open end and a closed end;
a plug having a lower end portion adapted to fit within and seal said open end of said blood collection tube, said plug having an underside substantially spanning said blood collection tube upon fitting the lower end portion of said plug therein;
a vacuum tube extended through said plug for evacuating air from said blood collection tube, said vacuum tube having an upper end and a lower end opening through the underside of said plug;
a pickup tube protruding outwardly from said plug for drawing blood from a puncture site;
a drop tube extending downwardly from said plug and having a lower end positioned within the blood collection tube and spaced substantially below the lower end of the vacuum tube;
conduit means within said plug for connecting said pickup tube and drop tube so that blood drawn into said pickup tube is deposited in the blood collection tube through the lower end of the drop tube;
a portable hand-held vacuum source including an inlet port;
means for connecting said inlet port to the upper end of said vacuum tube for creating a vacuum within said blood collection tube;
a primary filter comprising a hydrophobic porous membrane operative to allow gas flow therethrough but to block liquid flow therethrough;
sealing means for sealing said primary filter against the underside of said plug such that all air drawn into said vacuum tube from said collection tube must flow through said primary filter;
said lower end portion comprising a generally tubular member having a divider wall extended thereacross to form a pair of passages therethrough, one passage comprising the lower end of said vacuum tube and the other passage comprising said conduit means, said sealing means being operative to seal said primary filter against said divider wall and generally tubular member; and
said underside of said plug including a peripheral ridge circumscribing said lower end of said vacuum tube and conduit means, said sealing means securing said primary filter against said peripheral ridge.

7. The blood collection apparatus of claim 6 wherein said lower end portion of the plug further comprises a peripheral collar protruding generally axially from the underside of said plug and circumscribing said ridge to shield said primary filter from contact with the blood collection tube.

8. A blood collection apparatus comprising:
a blood collection tube having an open end and a closed end;
a plug having a lower end portion adapted to fit within and seal said open end of said blood collection tube, said plug having an underside substantially spanning said blood collection tube upon fitting the lower end portion of said plug therein;
a vacuum tube extended through said plug for evacuating air from said blood collection tube, said vacuum tube having an upper end and a lower end opening through the underside of said plug;
a pickup tube protruding outwardly from said plug for drawing blood from a puncture site;
a drop tube extending downwardly from said plug and having a lower end positioned within the blood collection tube and spaced substantially below the lower end of the vacuum tube;
conduit means within said plug for connecting said pickup tube and drop tube so that blood drawn into said pickup tube is deposited in the blood collection tube through the lower end of the drop tube;
a portable hand-held vacuum source including an inlet port;
means for connecting said inlet port to the upper end of said vacuum tube for creating a vacuum within said blood collection tube;
a primary filter comprising a hydrophobic porous membrane operative to allow gas flow therethrough but to block liquid flow therethrough;
sealing means for sealing said primary filter against the underside of said plug such that all air drawn into said vacuum tube from said collection tube must flow through said primary filter;
a secondary filter operatively interposed between said upper end of said vacuum tube and said inlet port of said vacuum source, said secondary filter comprising a filter disk of a hydrophobic porous membrane and being operative to allow gas flow therethrough but to block liquid flow therethrough, thus further filtering air drawn through said vacuum tube; and
said secondary filter comprising a replaceable filter cartridge having an inlet port connected to said vacuum tube of said plug, an outlet port connected to said inlet port of said vacuum source and a filter disk interposed between said inlet and outlet ports such that air drawn through said inlet port into said vacuum source passes through said filter disk.

9. The blood collection apparatus of claim 8 wherein said portable hand-held vacuum source comprises a housing, a vacuum pump mounted within said housing and operative to draw air through said inlet port and a bleeder port through said housing and positioned to establish fluid communication between said inlet port and ambient atmosphere in the absence of the secondary filter thereby rendering said blood collection apparatus inoperative in the absence of the secondary filter.

10. The blood collection apparatus of claim 9 wherein said vacuum pump comprises an electric motor, means for supporting battery means within said housing and circuitry for connecting said electric motor to battery means.

11. The apparatus of claim 10 wherein said circuitry comprises an externally accessible trigger switch operative to actuate said vacuum pump.

* * * * *